United States Patent [19]
Moreno

[11] Patent Number: 6,034,262
[45] Date of Patent: Mar. 7, 2000

[54] METHOD FOR THE PREPARATION OF CARBONATES BY A CONTINUOUS PROCESS

[75] Inventor: Phillip Moreno, Dalton, Mass.

[73] Assignee: General Electric Company, Schenectady, N.Y.

[21] Appl. No.: 09/218,651

[22] Filed: Dec. 22, 1998

[51] Int. Cl.⁷ .................................................. C07C 68/00
[52] U.S. Cl. ...................... 558/274; 558/271; 558/272; 558/273
[58] Field of Search .................... 558/274, 273, 558/272, 271

[56] References Cited

U.S. PATENT DOCUMENTS

| | | |
|---|---|---|
| 4,187,242 | 2/1980 | Chalk . |
| 5,229,482 | 7/1993 | Brunelle . |
| 5,231,210 | 7/1993 | Joyce et al. . |
| 5,239,103 | 8/1993 | Seltzer et al. . |
| 5,284,964 | 2/1994 | Pressman et al. . |
| 5,312,955 | 5/1994 | Pressman et al. . |
| 5,399,734 | 3/1995 | King, Jr. et al. . |
| 5,498,789 | 3/1996 | Takagi et al. . |
| 5,726,340 | 3/1998 | Takagi et al. . |
| 5,760,272 | 6/1998 | Pressman et al. . |

*Primary Examiner*—Michael G. Ambrose

[57] ABSTRACT

A continuous flow process for converting hydroxyaromatic compounds to diaryl carbonates by reaction with oxygen and carbon monoxide in the presence of a catalyst system typically comprising a group VIIIB metal or compound thereof, an inorganic co-catalyst, an organic co-catalyst and a hexaalkylguanidinium bromide or chloride, preferably bromide, wherein at least two components of the catalyst system, preferably lead oxide and hexaalkylguanidinium bromide, are introduced separately into the reactor.

18 Claims, 3 Drawing Sheets

METHOD FOR THE PREPARATION OF CARBONATES BY A CONTINUOUS PROCESS

BACKGROUND OF THE INVENTION

This invention relates to a preparation of diaryl carbonates by direct oxidative carbonylation. More particularly, it relates to the methods for the production of diaryl carbonates by continuous processes.

Diaryl carbonates, and diphenyl carbonate in particular, are valuable monomer precursors for the preparation of polycarbonates by melt transesterification. An advantageous route for the synthesis of diaryl carbonates is the direct carbonylation of aromatic compounds by carbon monoxide and oxygen in the presence of a catalyst.

A wide range of catalysts may be used. For example, U.S. Pat. No. 4,187,242 to Chalk discloses catalysts derived from Group VIIIB metals, i.e., metals selected from the group consisting of ruthenium, rhodium, palladium, osmium, iridium and platinum, or complexes thereof. U.S. Pat. No. 5,231,210 to Joyce, U.S. Pat. No. 5,284,964 to Pressman et al., U.S. Pat. No. 5,760,272 to Pressman and U.S. Pat. No. 5,399,734 to King, Jr., et al. further disclose the use of co-catalysts, including metal co-catalyst species such as cobalt pentadentate complexes and other cobalt(II) complexes with pyridines, bipyridines, terpyridines, quinolines; aliphatic polyamines, crown ethers, aromatic or aliphatic amine ethers, and Schiff bases. These metal co-catalysts are often used in combination with organic co-catalysts such as terpyridines and halide sources such as quaternary ammonium or phosphonium halides.

One catalyst system of particular interest is disclosed in U.S. Pat. No. 5,498,789 to Takagi et al. The catalyst system consists of palladium or a palladium compound, at least one lead compound, at least one halide selected from quaternary ammonium halides and quaternary phosphonium halides, and optionally at least one copper compound. Use of a lead co-catalyst yields a process wherein the yield of aromatic carbonate per equivalent of palladium (turnover number of palladium) is high, i.e. greater than about 700. A further improved catalyst system comprises use of hexaalkylguanidinium halides, particularly hexaethylguanidinium bromide, as a halide source. Use of hexaalkylguanidinium halides in amounts essentially equivalent to the amounts of quaternary ammonium halides previously employed leads to significant increases in yield of product (i.e., percentage of hydroxyaromatic compound converted to reaction products).

Despite the potential of the foregoing catalyst system in the direct carbonylation of aromatic hydroxy compounds, there remain certain drawbacks and disadvantages from the standpoint of commercialization, most notably that prior disclosures are directed to batch or batch-flow reactions on small scales. "Batch-flow" processes are disclosed, for example in U.S. Pat. No. 5,399,734 to King et al. In a batch-flow process the reactor is charged with aromatic organic hydroxy compound and catalyst while the oxygen and carbon monoxide are introduced and maintained at constant partial pressures and total pressures. Both batch and batch-flow processes are not economic on commercial scales, and a commercial process for the production of diaryl carbonates should accordingly be adapted in to a continuous flow process.

Such adaptation is not always straightforward. A case in point is adaptation of diaryl carbonate production using the above-described palladium/lead oxide/hexaalkylguanidinium halide catalyst system using continuous flow reactor system 10 shown schematically in FIG. 1. A solution of lead oxide (PbO) and Pd(acetylacetonate)$^2$ in phenol from tank 12 is fed via conduit 16 into common conduit 20. Hexaalkylguanidinium halide in phenol is fed from tank 14 via conduit 18 into common conduit 20. Common conduit 20 feeds the mixture of co-catalysts into reactor 22. However, use of this continuous process system resulted in significantly lower yields than those obtained in batch or batch-flow processes. Accordingly, there remains a need in the art for methods and apparatus for the production of diaryl carbonates by direct carbonylation using continuous flow processes.

SUMMARY OF THE INVENTION

The above-described drawbacks and disadvantages of the prior art are overcome or alleviated by the present method for continuous flow production of diaryl carbonates, comprising contacting an aromatic hydroxy compound with oxygen and carbon monoxide in the presence of a catalyst system in a continuous flow reactor, wherein at least two of the catalyst system components are introduced into the continuous flow reactor separately. Use of this method allows commercial scale production of diphenyl carbonates by direct carbonylation.

DETAILED DESCRIPTION OF THE INVENTION

Figure 1:
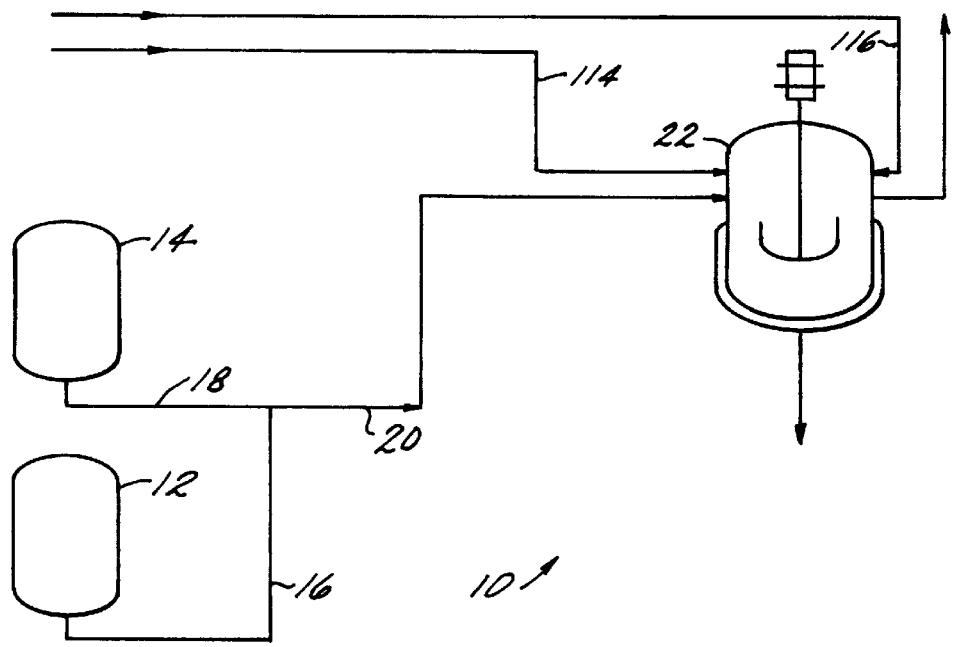
FIG. 1 is a schematic diagram of a prior art system for continuous flow production of diaryl carbonates.

The present method for continuous flow production of diaryl carbonates comprises contacting an hydroxyaromatic compound with oxygen and carbon monoxide in the presence of a catalyst system in a continuous flow reactor, wherein at least two of the catalyst system components are introduced into the continuous flow reactor separately. In a preferred embodiment, the catalyst system comprising an effective amount of catalyst, a lead compound, and a hexaalkylguanidinium halide, wherein the lead compound and the hexaalkylguanidinium halide are introduced into the continuous flow reactor separately. Use of this method allows commercial scale production of diphenyl carbonates by direct carbonylation.

A broad range of hydroxyaromatic compounds may be employed in the present invention including monocyclic, polycyclic, or fused polycyclic aromatic hydroxy compounds. Monohydroxyaromatic compounds, such as phenol, the cresols, the xylenols, naphthol, and p-cumylphenol, are generally preferred, with phenol being most preferred. The invention may, however, also be employed with dihydroxyaromatic compounds such as resorcinol, the various isomers of dihydroxynaphthalene, hydroquinone and 2,2-bis (4-hydroxyphenyl)propane or "bisphenol A", whereupon the products are polycarbonates.

Other essential reagents in the method of this invention are oxygen and carbon monoxide, which react with the hydroxyaromatic compound to form the desired diaryl carbonate. The carbon monoxide may be high-purity carbon monoxide or carbon monoxide diluted with another gas such as nitrogen, argon, carbon dioxide, or hydrogen, which have no negative effects on the reaction. The oxygen used in the present invention may be high-purity oxygen, air, or oxygen diluted with another gas such as nitrogen, argon, or carbon dioxide that have no negative effects on the reaction.

The catalyst system comprises a catalyst, at least one metal cocatalyst, an optional organic co-catalyst, and an optional halide source, preferably a hexaalkylguanidinium halide. The catalyst is a catalytically effective Group VIIIB metal, preferably palladium or a palladium compound. Thus, palladium black or elemental palladium deposited on carbon or silica are suitable, as well as palladium compounds such as halides, nitrates, carboxylates and complexes of palladium with carbon monoxide, amines, phosphines or olefins. Preferred compounds include palladium(II) salts of organic acids, for example aliphatic carboxylic acids having from 2 to 6 carbons, and palladium(II) salts of β-diketones such as 2,4-pentanedione. Palladium(II) acetate [$Pd(OC(O)CH_3)_2$] and palladium(II) 2,4-pentanedionate ($Pd(acac)_2$) are generally most preferred.

The catalyst system preferably also includes an inorganic co-catalyst, and/or an organic co-catalyst of the type disclosed in the aforementioned U.S. Pat. No. 5,284,964, which is incorporated by reference herein. Thus preferred inorganic co-catalysts include divalent or trivalent manganese halide or carboxylate salts, or amine, diketone, or carbon monoxide complexes; or cobalt(II) halide or carboxylate salts, or amine, diketone, or carbon monoxide complexes, for example cobalt chloride and cobalt acetate. Also useful are cobalt(II) salts of the type disclosed in the aforementioned U.S. Pat. No. 5,231,210; namely, complexes of cobalt(II) salts with organic compounds capable of forming complexes, especially pentadentate complexes, therewith. Illustrative organic compounds of this type are nitrogen-heterocyclic compounds including pyridines, bipyridines, terpyridines, quinolines, isoquinolines, and biquinolines; aliphatic polyamines such as ethylenediamine and tetraalkylethylenediamines; crown ethers; aromatic or aliphatic amine ethers such as cryptanes; and Schiff bases. An especially preferred inorganic co-catalyst is a cobalt(II) complex with bis[3-(salicylalamino)propyl]methylamine, this complex hereinafter being designated "CoSMDPT".

Other inorganic co-catalysts include various lead compounds. The lead compounds are preferably soluble in a liquid phase under the reaction conditions. Examples of such lead compounds include lead oxides for example PbO, $Pb_3O_4$, and $PbO_2$; lead carboxylates, for example $Pb(OC(O)CH_3)_2$, $Pb(OC(O)CH_3)_4$, and $Pb(OCOC_2H_5)_2$; lead salts such as $Pb(NO_3)_2$ and $PbSO_4$; and alkoxy and aryloxy lead salts such as $Pb(OCH_3)_2$, and $Pb(OC_6H_6)_2$; and lead complexes such as phthalocyanine lead and the like. Of these compounds, lead oxides and lead compounds represented by formula $Pb(OR)_2$ wherein R is an aryl group having from six to ten carbons, or an acyl group having an alkyl group with one to four carbons are preferred.

Suitable organic co-catalysts which may be employed include various terpyridine, phenanthroline, quinoline and isoquinoline compounds including 2,2':6'2"-terpyridine, 4'-methylthio-2,2':6',2"-terpyridine and 2,2':6',2"-terpyridine N-oxide, 1,10-phenanthroline, 2,4,7,8-tetramethyl-1,10-phenanthroline, 4,7-diphenyl-1,10, phenanthroline and 3,4,7,8-tetramethyl-1,10-phenanthroline. The terpyridines, and especially 2,2':6',2"-terpyridine, are generally preferred.

The chloride or bromide, preferably bromide, source employed according to the present invention is tertiary ammonium chloride or bromide, a hexaalkylguanidinium chloride or bromide of the type disclosed in U.S. Pat. No. 5,229,482, the disclosure of which is incorporated by reference herein. Included are the α,ω-bis (pentaalkylguanidinium)alkane salts. Chlorides or bromides in which the alkyl groups contain two to six carbon atoms are preferred, with hexaethylguanidinium bromide being especially preferred.

The proportion of Group VIIIB metal source employed is typically in the range of about 5–800 ppm by weight of metal, based on hydroxyaromatic compound. Thus, both "high concentration" systems in which the level of Group VIIIB metal is in the range of about 100–800 ppm, and "low concentration" systems in which it is in the range of about 5–100 ppm, are within the scope of the invention.

In the "high concentration" system, for each equivalent of Group VIIIB metal there is usually employed about 0.1–5.0 or from about 0.5–1.5 gram-atoms of metal co-catalyst (i.e., cobalt or manganese), about 0.1–3.0 and preferably about 0.3–1.0 moles of organic co-catalyst, and about 2–150, preferably about 5–40, moles of hexaalkylguanidinium halide.

In the "low concentration" system, lead is typically present in the amount of about $10^{-4}$ to about $10^{-1}$, preferably about $10^{-4}$ to about $10^{-2}$, mole per mole of hydroxyaromatic compound. For each equivalent of Group VIIIB metal, i.e., palladium, there is usually employed about 1000–5000, preferably about 2500–3500, molar equivalents of hexaalkylguanidinium halide with respect to Group VIIIB metal.

Gas is supplied to the reaction mixture in proportions of about 2–50 mole percent oxygen, with the balance being carbon monoxide. The gases may be introduced separately or as a mixture, to a total pressure in the range of about 10–250 atmospheres. Reaction temperatures in the range of about 60–150° C. are typical. Dryings agents, typically molecular sieves, may be present in the reaction vessel. In order for the reaction to be as rapid as possible, it is preferred to maintain the reaction pressure, i.e., maintain essentially constant partial pressures of oxygen in accordance with the aforementioned U.S. Pat. No. 5,399,734 until conversion of the hydroxyaromatic compound is complete.

In prior art continuous flow processes, catalyst feed systems, solutions of different catalyst system components are stored separately, and then pumped from tanks which join into a single line immediately. They then flow as a mixture to the reactor and are mixed with the gaseous reactants. Adaptation of such systems to reactions employing the palladium/lead/halide source catalyst system is shown in FIG. 1, wherein a solution of lead oxide (PbO) in phenol from tank 12 is fed via conduit 16 into common conduit 20. Hexaalkylguanidinium halide in phenol is fed from tank 14 via conduit 18 into common conduit 20. Common conduit 20 feeds the mixture of co-catalysts into reactor 22.

It has been found that use of this continuous process system results in significantly lower yields than those obtained in batch or batch-flow processes. These failures were particularly surprising, in that tests of the crude reaction mixture after reaction indicated that soluble lead was present at the theoretical concentration. The inventors hereof have unexpectedly found that mixtures of components such as lead(II) oxide and hexaethylguanidinium bromide fed through approximately 20 feet of feet-traced quarter inch tubing results in formation of insoluble precipitant. This insoluble precipitant prevents efficient continuous flow operation and produces inconsistent yields of diphenyl carbonate. Solubility experiments demonstrate that at 60° C., lead oxide is soluble in phenol in concentrations of up to at least 17,000 ppm of lead. However, addition of 790 ppm of lead oxide to a five percent hexaethylguanidinium bromide solution in phenol at 80° C. results in formation of a white precipitate, and a concentration of lead in solution of only 320 ppm of lead (as determined by atomic absorption spectrophotometry). Increasing the temperature to 110° C. results in increasing the quantity of soluble lead to only 520 ppm. These data indicate that in contrast to the reaction mixtures, simple mixing of a hexaethylguanidinium bromide/phenol solution with a lead oxide/phenol solution results in a reduced concentration of soluble lead, which cannot be increased to theoretical concentration by heating.

Accordingly, the present continuous process comprises separate storage and transport of at least two of the catalyst system components. Preferably, one of a lead/phenol solution or hexaethylguanidinium bromide/phenol solution is stored in a first tank and the other stored in a second tank. Use of separate feed lines prevents mixing until its components reach the reactor where they simultaneously mix with the gaseous reactants.

Figure 2:
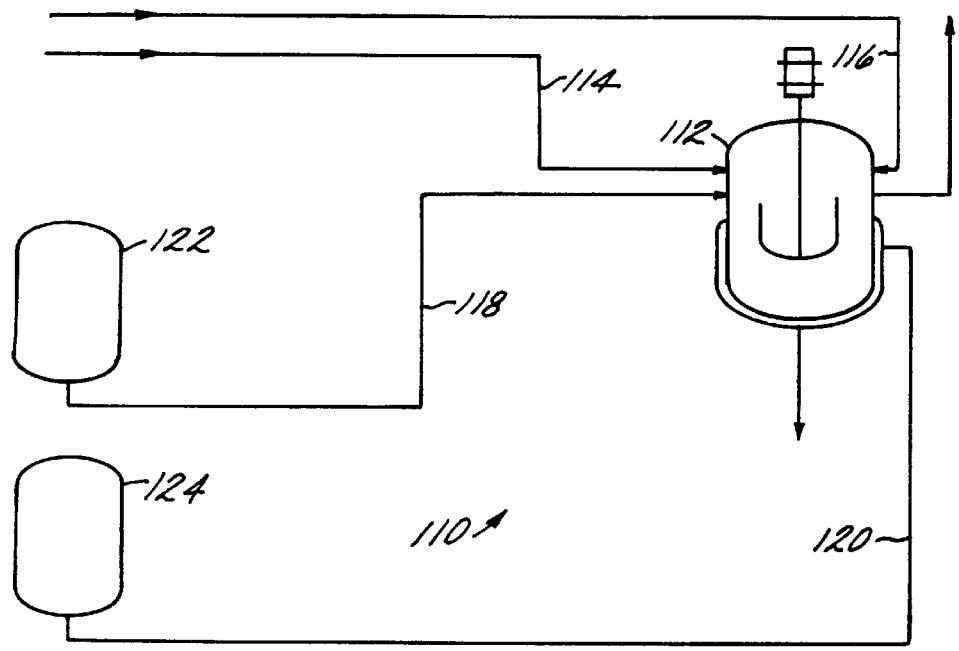
FIG. 2 is a schematic diagram of a system suitable for use with the present method.

In order that those of ordinary skill in the art will be better able to practice a preferred form of the method, reference is made to the drawings. FIG. 2 shows a schematic of a continuous reactor system for preparing aromatic organic carbonate, capable of delivering a continuous flow at a rate of about 50 mL to 1000 mL and preferably about 300 mL to 600 mL per minute, wherein a mixture of carbon monoxide and oxygen is maintained at a substantially constant molar ratio and partial pressures of oxygen and carbon monoxide. More particularly there is shown at 110 a reactor 112 having gaseous input feed lines 114, 116 and two separate catalyst input feed lines 118, 120. Line 118 is a feed line from tank 122 holding one of the halide source or the lead compound, and line 120 is feed line for tank 124 holding the other. Appropriate quantities of the halide source and lead compound are fed into reactor 112 via feed lines 118, 120, and mixed upon entry into reactor 112. Yield of diphenyl carbonate using this configuration is similar to that seen for batch-flow processes.

Figure 3:
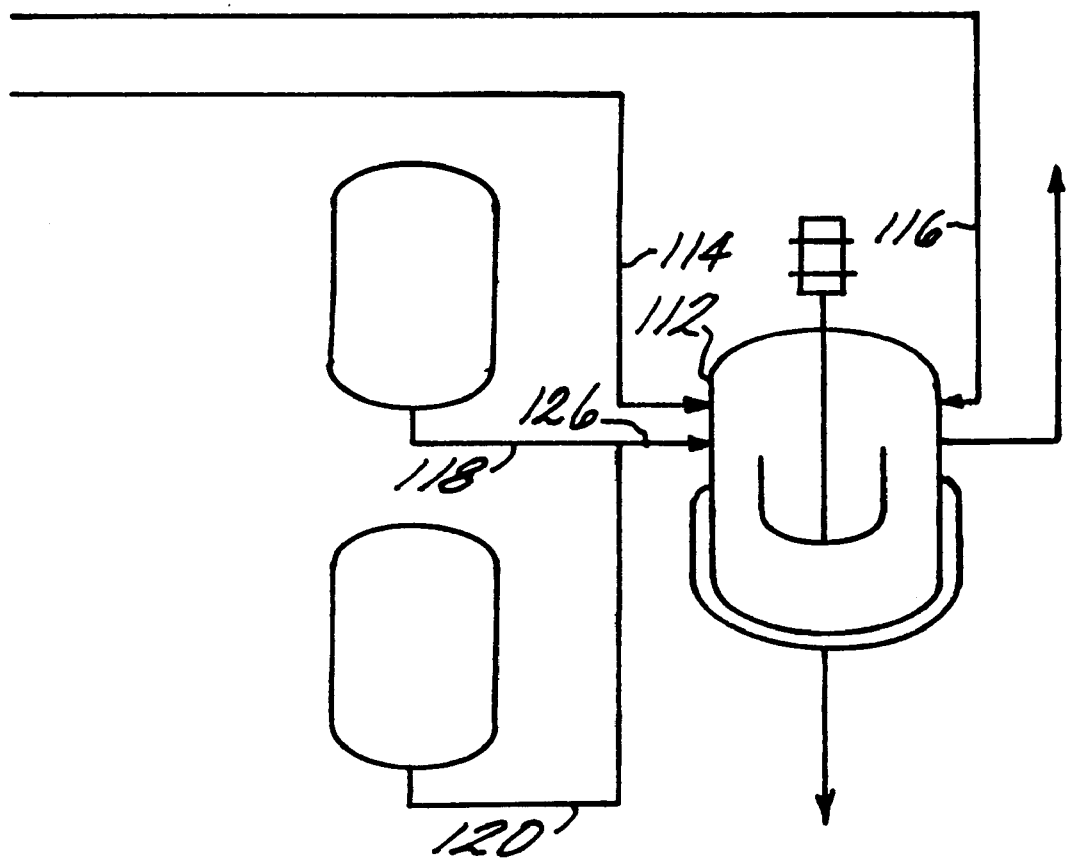
FIG. 3 is a schematic diagram of an alternative embodiment in accordance with the present method.
Figure 4:
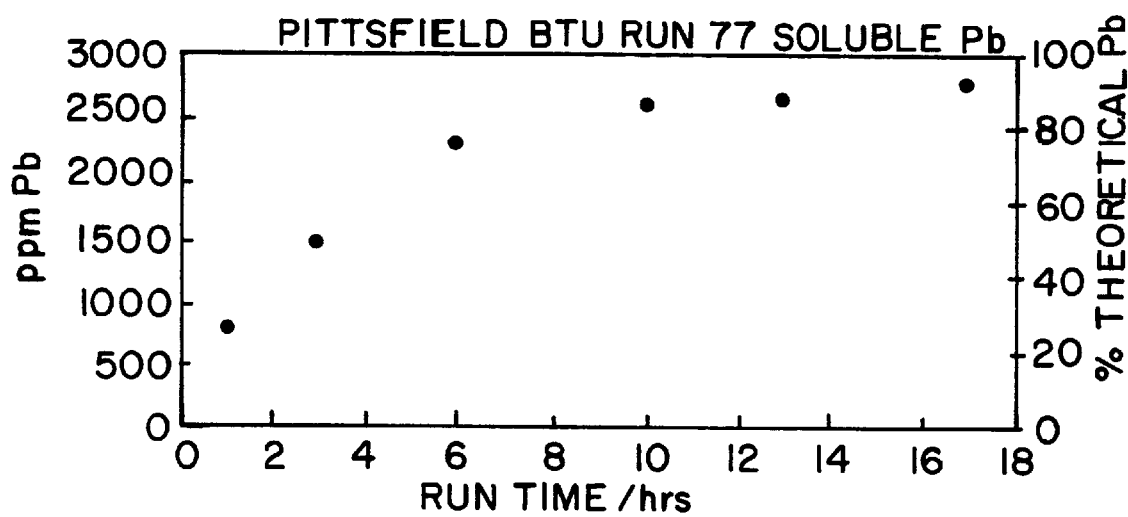
FIG. 4 is a graph showing the percent of soluble lead oxide present over time in the crude reaction mixture of the present method.

An alternative embodiment of the present invention is shown at FIG. 3, wherein feed lines 118, 120 feed into a single line 126, which feeds into reactor 112. In an important feature of this embodiment, the length of feed line 126 is extremely short, such that no or substantially no precipitate forms prior to entry into tank 112. Preferably, the width of feed line 126 is such that any precipitate formed does not result in substantial blockage of the line, thereby allowing feed into reactor 112 at steady, predictable rates. Length of feed line 126 is determined primarily based on the speed of precipitate formation and width of the feed line, wherein fast precipitate requires short, wide lines so as to prevent blockage. This embodiment provides at least partial mixing of the catalyst components prior to their introduction into reactor 112.

The diaryl carbonates produced by the method of this invention may be isolated by conventional techniques. It is often preferred to form and thermally crack an adduct of the diaryl carbonate with the hydroxyaromatic compound, as described in U.S. Pat. Nos. 5,239,103 and 5,312,955.

The method is further illustrated by the following non-limiting examples.

EXAMPLE 1

Figure 5:
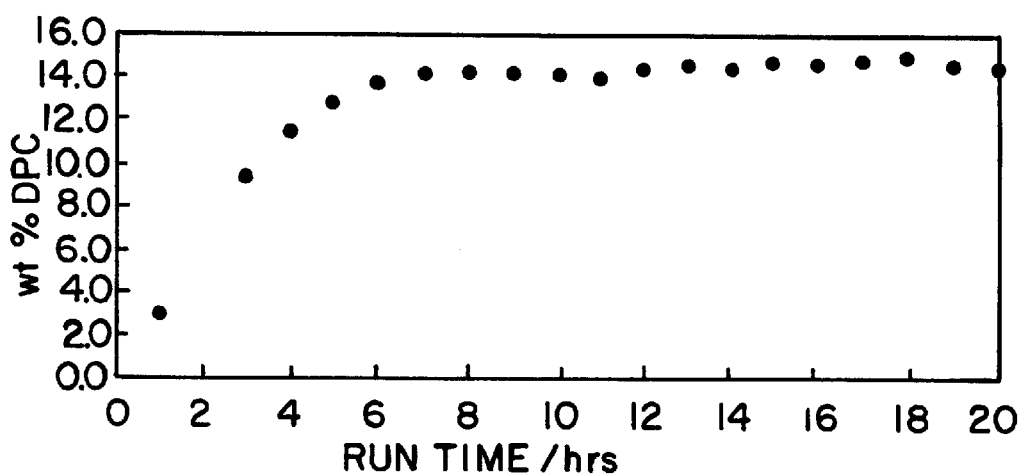
FIG. 5 is a graph showing the yield of diphenyl carbonate over time in a continuous process in accordance with the present method.

A phenolic solution (feedstream A) was prepared consisting of 2.50 grams Pd(acac)$_2$ (8.20 mmol), 112.80 grams PbO (505.8 mmol; 61.7 equivalents of lead per equivalent of palladium) in 16.0 liters of phenol. A second phenolic solution (feedstream B) was prepared consisting of 1767 grams hexaethylguanidinium bromide (5775 mil) in 14.2 liters of phenol. Each feedstream was maintained at 65° C. and pumped at a rate of 0.6 liters/hour into a stirred, 1-gallon continuous reactor system maintained at 65° C. and 40 psig. Once the reactor was filled, gas flow of a mixture consisting of 6% oxygen in carbon monoxide was initiated at a rate of 1200 SLPH (standard liters per hour) to achieve a pressure of 1200 psig, after which the reactor temperature was increased to 100° C. These conditions (100° C., 1200 psig, 1200 SLPH of 6% oxygen in carbon monoxide gas mixture, with stirring) were maintained for approximately 20 hours, and weight percent of diphenol carbonate was determined by high pressure liquid chromatography over the course of the reaction. Yield of diphenyl carbonate over time is shown graphically in FIG. 5, which illustrates that high yields (approx. 14 weight %) of diphenyl carbonate are maintained after even 20 hours of reaction under continuous flow conditions. Quantity of soluble lead oxide in the reaction mixture was initially low, but approached about 90% of the theoretical quantity after about 8 hours, as shown in FIG. 5.

EXAMPLE 2 (COMPARATIVE)

A phenolic solution (feedstream A) was prepared consisting of 1.7849 g Pd(acac)$_2$ (5.86 mmol), 20.14 g PbO (90.2 mmol; 15.4 equivalents of lead per equivalent of palladium) and 11.4 liters of phenol. A second phenolic solution (feedstream B) was prepared consisting of 1261 g hexaethylguanidinium bromide (4112 mmol) in 3.2 liters of phenol. Each feedstream was maintained at 65° C. and pumped at a rate of 1.5 liters/hour into a stirred, 1-gallon continuous reactor system, maintained at 65° C. and 40 psig. Once the reactor was filled, gas flow of a mixture consisting of 6% oxygen in carbon monoxide was initiated at a rate of 1200 SLPH to achieve a pressure of 1200 psig, after which the reactor temperature was increased to 100° C. These conditions (100° C., 1200 psig, 1200 SLPH of 6% oxygen in carbon monoxide gas mixture, with stirring) were maintained for approximately 7 hours, and weight percent of diphenyl carbonate was determined by high pressure liquid chromatography over the course of the reaction. Only 1.5–2 weight % of diphenol carbonate was produced after 7 hours. A similar batch flow reaction run under the same pressure and oxygen concentration produced 17% diphenyl carbonate in 1.25 hours.

EXAMPLE 3 (COMPARATIVE)

A phenolic solution (feedstream A) was prepared consisting of 1.2500 g Pd(acac)$_2$ (4.104 mmol), 14.10 g PbO (63.17 mmol; 15.4 equivalents of lead per equivalent of palladium) and 8.0 liters of phenol. A second phenolic solution (feedstream B) was prepared consisting of 884.0 g hexaethylguanidinium bromide (2889 mmol) in 7.2 liters of phenol. Each feedstream was maintained at 65° C. and pumped at a rate of 0.4 liters/hour into a stirred, 1-gallon continuous reactor system, maintained at 60° C. and 40 psig. The run was aborted due to white precipitate plugging a flow meter, which measures the flow of catalyst solution after mixing of feedstreams A and B.

In contrast to Example 2 and 3, introducing HEGBr/phenol and lead oxide phenol solution separately into a reactor results in production of up to 14% diphenol carbonate by weight after six hours (FIG. 2).

While preferred embodiments have been shown and described, various modifications and substitutions may be made thereto without departing from the spirit and scope of the invention. Accordingly, it is to be understood that the present invention has been described by way of illustration and not limitation.

I claim:

1. A method for the synthesis of a diaryl carbonate by a continuous process by contacting at least one hydroxyaromatic compound with oxygen and carbon monoxide in the presence of catalyst system comprising a Group VIIIB metal catalyst, an inorganic co-catalyst, an optional organic catalyst, and at least one halide source, comprising providing a first solution comprising at least one first catalyst system component in a first tank having a first feed;

providing a second solution comprising at least one second catalyst system component in a second tank having a second feed; and feeding the first and second solutions into a reactor via the first and second feeds without substantial precipitate formation in the feeds which interfere with substantially continuous flow into the reactor.

2. The method of claim 1, wherein the first and second feeds are completely physically separate from each other.

3. The method of claim 1, wherein the first and second feeds join to form a third feed into the reactor, wherein the length of the third feed is insufficient to allow substantial precipitate formation.

4. The method of claim 3, wherein the length of the third feed is insufficient to allow precipitate formation.

5. The method of claim 3, wherein the length and width of the third feed allow substantially continuous flow into the reactor.

6. The method of claim 1, wherein the Group VIIIB metal is palladium or a palladium compound, the inorganic co-catalyst is a lead compound, and the halide source is a hexaalkylguanidinium chloride, a hexaalkylguanidinium bromide, an α,ω-bis(pentaalkylguanidinium) alkane salt, a tertiary alkylammonium chloride, or a tertiary ammonium bromide.

7. The method of claim 6 wherein the palladium or palladium metal compound is selected from the group consisting of palladium black, elemental palladium deposited on carbon, elemental palladium deposited on silica, palladium halides, palladium nitrates, palladium carboxylates, and complexes of palladium with carbon monoxide, amines, phosphines or olefins.

8. The method of claim 7 wherein palladium compound is selected from the group consisting of palladium(II) acetate, palladium(II) 2,4-pentanedionate, a palladium(II) salt of a β-diketone, and a palladium(II) salt of an aliphatic carboxylic acid having from 2 to 6 carbons.

9. The method of claim 7, wherein the lead compound is selected from the group consisting of lead oxides, PbO, $Pb_3O_4$, $PbO_2$; lead carboxylates, $Pb(OC(O)CH_3)_2$, $Pb(OC(O)CH_3)_4$, $Pb(OCOC_2H_5)_2$; lead salts, $Pb(NO_3)_2$, $PbSO_4$, alkoxy lead salts, aryloxy lead salts, $Pb(OCH_3)_2$, $Pb(OC_6H_6)_2$, lead complexes, and phthalocyanine.

10. The method of claim 9, wherein the lead compound is selected from the group consisting of lead oxides and $Pb(OR)_2$ wherein R is an aryl group having from six to ten carbons, or an acyl group having an alkyl group with one to four carbons.

11. The method of claim 7 wherein the alkyl groups in the hexaalkylguanidinium chloride or bromide or the tertiary ammonium chloride or bromide have from two to six carbon atoms.

12. The method of claim 11 wherein the hexaalkylguanidinium halide is hexaethylguanidinium bromide.

13. The method of claim 1 wherein the hydroxyaromatic compound is selected from the group consisting phenol, cresols, xylenols, naphthol, p-cumylphenol, resorcinol, isomers of dihydroxynaphthalene, hydroquinone and 2,2-bis(4-hydroxyphenyl)propane.

14. The method of claim 11, wherein the hydroxyaromatic compound is phenol.

15. The method of claim 1, wherein the first solution comprises the Group VIIIB metal catalyst and the metal co-catalyst, and the second solution comprises the halide source.

16. The method of claim 1, wherein the first solution comprises palladium or a palladium compound, and the second solution comprises a hexaalkylguanidinium bromide.

17. The method of claim 14, wherein the palladium or palladium compound is selected from the group consisting of palladium(II) acetate, palladium(II) 2,4-pentanedionate, a palladium(II) salt of a β-diketone, and a palladium(II) salt of an aliphatic carboxylic acid having from 2 to 6 carbons, the lead compound is selected from the group consisting of lead oxides and $Pb(OR)_2$ wherein R is an aryl group having from six to ten carbons, or an acyl group having an alkyl group with one to four carbons, and the hexaalkylguanidinium halide is hexaethylguanidinium bromide.

18. A method for preparing a diaryl carbonate by a continuous flow process, comprising contacting at least one hydroxyaromatic compound with oxygen and carbon monoxide in the presence of a catalytic system comprising a Group VIIIB metal catalyst, an inorganic co-catalyst, an optional organic catalyst, and at least one hexaalkylguanidinium bromide or chloride, in a continuous flow reactor, wherein at least two of the catalytic system components are introduced into the continuous flow reactor separately from each other.

* * * * *